(12) United States Patent
Kimura et al.

(10) Patent No.: US 8,551,086 B2
(45) Date of Patent: Oct. 8, 2013

(54) ENDOSCOPIC TREATMENT TOOL

(75) Inventors: Megumi Kimura, Tokyo (JP); Keita Suzuki, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 318 days.

(21) Appl. No.: 13/150,585

(22) Filed: Jun. 1, 2011

(65) Prior Publication Data

US 2012/0029507 A1    Feb. 2, 2012

Related U.S. Application Data

(63) Continuation of application No. PCT/JP2010/063182, filed on Aug. 4, 2010.

(30) Foreign Application Priority Data

Sep. 15, 2009   (JP) ................................ P2009-212942

(51) Int. Cl.
    *A61B 18/14*    (2006.01)
(52) U.S. Cl.
    USPC .......................................................... 606/41
(58) Field of Classification Search
    USPC ........ 606/27, 34, 41, 45, 46, 51, 52, 205–207
    See application file for complete search history.

(56) References Cited

U.S. PATENT DOCUMENTS

| | | |
|---|---|---|
| 2002/0143358 A1 | 10/2002 | Domingo et al. |
| 2009/0112229 A1 | 4/2009 | Omori et al. |

FOREIGN PATENT DOCUMENTS

| | | |
|---|---|---|
| EP | 2 098 170 A2 | 9/2009 |
| JP | 09-192136 | 7/1997 |
| JP | 11-104137 | 4/1999 |
| JP | 2004-321660 | 11/2004 |
| JP | 2008-246145 | 10/2008 |
| WO | 2009/067649 A2 | 5/2009 |

OTHER PUBLICATIONS

European Search Report dated May 6, 2013 from corresponding European Patent Application No. 10 816 987.1.
International Search Report dated Aug. 31, 2010.
Japanese Office Action dated May 17, 2011 together with English language translation.

*Primary Examiner* — Michael Peffley
*Assistant Examiner* — Daniel Fowler
(74) *Attorney, Agent, or Firm* — Scully, Scott, Murphy & Presser, P.C.

(57) ABSTRACT

Provided is an endoscope treatment tool including: a pair of clamp members that is supported by a clamp rotary shaft to be relatively rotatable; an operation section that is used to open and close the pair of clamp members; an operation wire that connects the pair of clamp members to the operation section; a connection member that is provided at the front end of the operation wire and includes at least one link rotary shaft; a pair of link members of which a first end is rotatably connected to each end of the pair of clamp members and a second end is rotatably connected to the link rotary shaft; and a regulation portion that regulates the connection member and the operation wire in a relative movement direction with respect to the clamp rotary shaft, wherein the connection member includes a groove formed to be parallel to the axis of the operation wire, and wherein the regulation portion engages with the groove to regulate the connection member and the operation wire in the relative movement direction.

4 Claims, 14 Drawing Sheets

US 8,551,086 B2

ENDOSCOPIC TREATMENT TOOL

BACKGROUND OF THE INVENTION

1. Field of the Invention

The present invention relates to an endoscope treatment tool that is used while being endoscopically inserted into a body cavity.

Priority is claimed on Japanese Patent Application No. 2009-212942, filed Sep. 15, 2009, the content of which is incorporated herein by reference.

2. Description of Related Art

Hitherto, an endoscope treatment tool (hereinafter, simply referred to as a "treatment tool") has been known which is used to perform various surgical operations on tissue inside a body cavity while being endoscopically inserted into the body cavity.

As an example of the treatment tool, a clamp disclosed in Japanese Patent No. 4197983 is known. The front end of the clamp is provided with a pair of clamp members supported through a rotary shaft to be relatively rotatable.

The pair of clamp members is connected to an operation section near the hand by an operation wire. Two link members are rotatably attached to the front end of the operation wire, and the front ends of the link members are respectively connected to one base end and the other base end of the pair of clamp members so as to be rotatable.

Accordingly, when the operation wire is made to move forward and backward in the axial direction through the operation section, the pair of clamp members may be opened and closed while relatively rotating about the rotary shaft.

SUMMARY OF THE INVENTION

According to one aspect of the invention, there is provided an endoscope treatment tool including: a pair of clamp members that is supported by a clamp rotary shaft to be relatively rotatable; an operation section that is used to open and close the pair of clamp members; an operation wire that connects the pair of clamp members to the operation section; a connection member that is provided at the front end of the operation wire and includes at least one link rotary shaft; a pair of link members of which a first end is rotatably connected to each end of the pair of clamp members and a second end is rotatably connected to the link rotary shaft; and a regulation portion that regulates the connection member and the operation wire in a relative movement direction with respect to the clamp rotary shaft, wherein the connection member includes a groove formed to be parallel to the axis of the operation wire, and wherein the regulation portion engages with the groove to regulate the connection member and the operation wire in the relative movement direction.

DETAILED DESCRIPTION OF THE INVENTION

Figure 1:
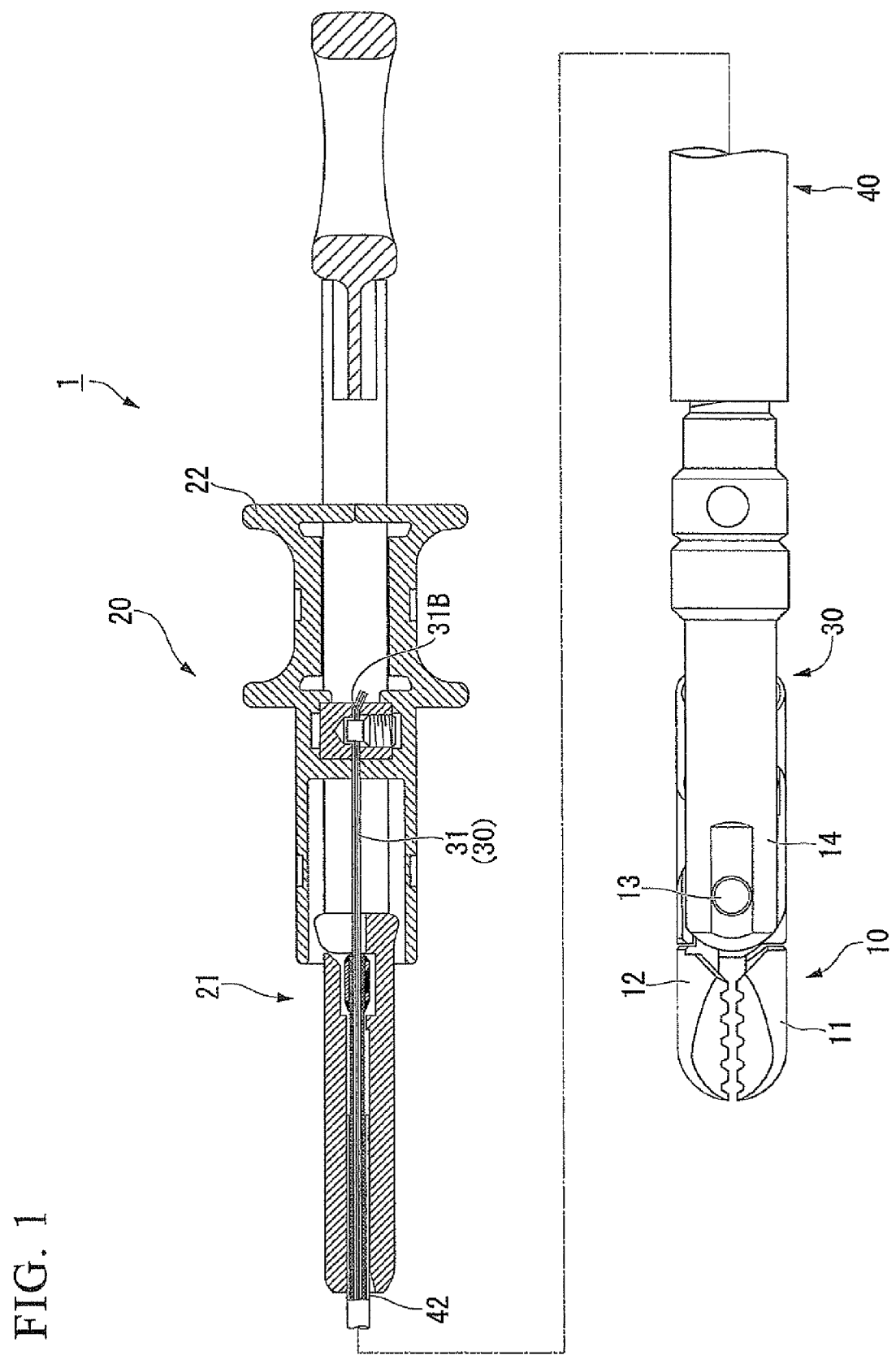
FIG. 1 is an overall diagram illustrating an endoscope treatment tool of a first embodiment of the invention.

Hereinafter, an endoscope treatment tool of a first embodiment of the invention will be described by referring to FIGS. 1 to 6. As shown in FIG. 1, a treatment tool 1 as the endoscope treatment tool of the embodiment includes: a treatment section 10 that is used to perform a treatment on tissue inside a body cavity, an operation section 20 that is used to operate the treatment section 10, a connection section 30 that is used to connect the treatment section 10 and the operation section 20 to each other, and an elongated insertion section 40 that is inserted into the body cavity.

In the treatment section 10, a pair of clamp members, that is, a first clamp member 11 and a second clamp member 12 that are rotatably supported to a clamp rotary shaft 13. The clamp rotary shaft 13 is supported to a cover 14 disposed with the clamp members 11 and 12 interposed therebetween.

The operation section 20 includes a body 21 to which the insertion section 40 is attached and a slider 22 that is slidably attached to the body 21.

The slider 22 and the treatment section 10 are connected to each other through the connection section 30, and when the slider 22 slides in the longitudinal direction of the body 21, the pair of clamp members 11 and 12 may be opened and closed. This point will be specifically described when explaining the operation in use.

Figure 2:
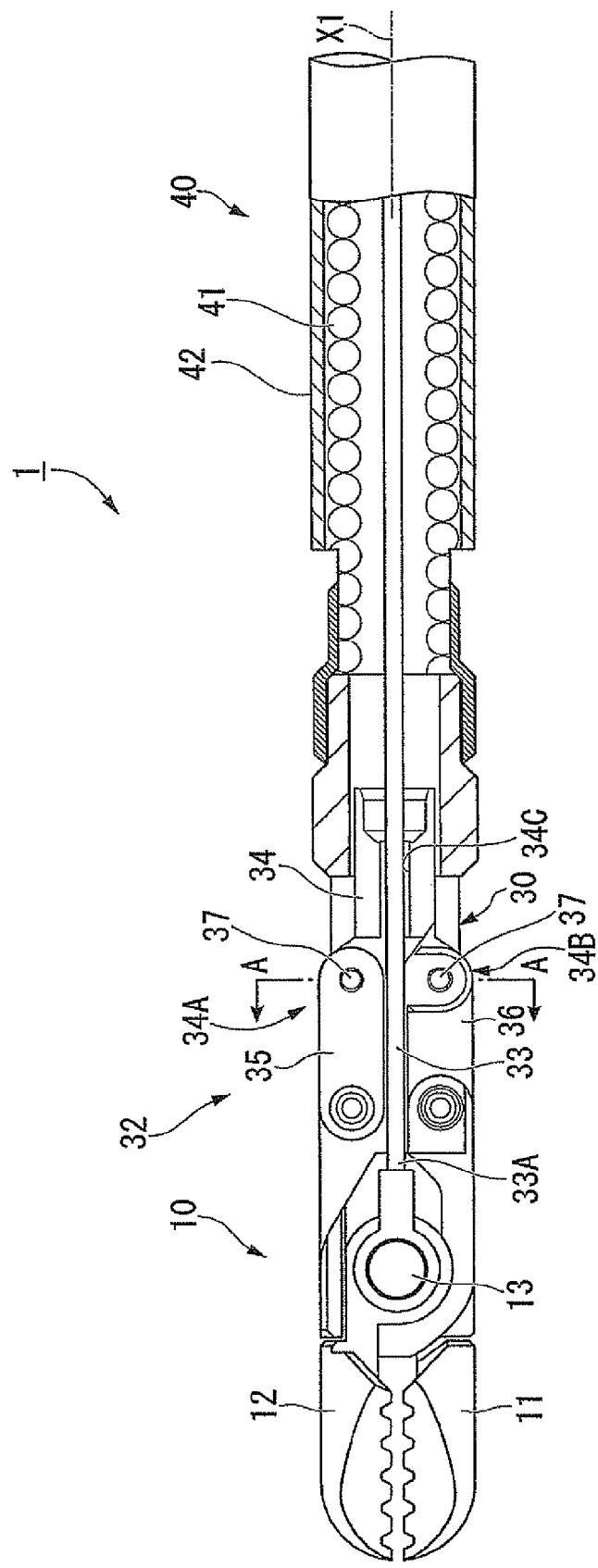
FIG. 2 is a diagram illustrating the vicinity of a treatment section of the endoscope treatment tool except for a cover.
Figure 3:
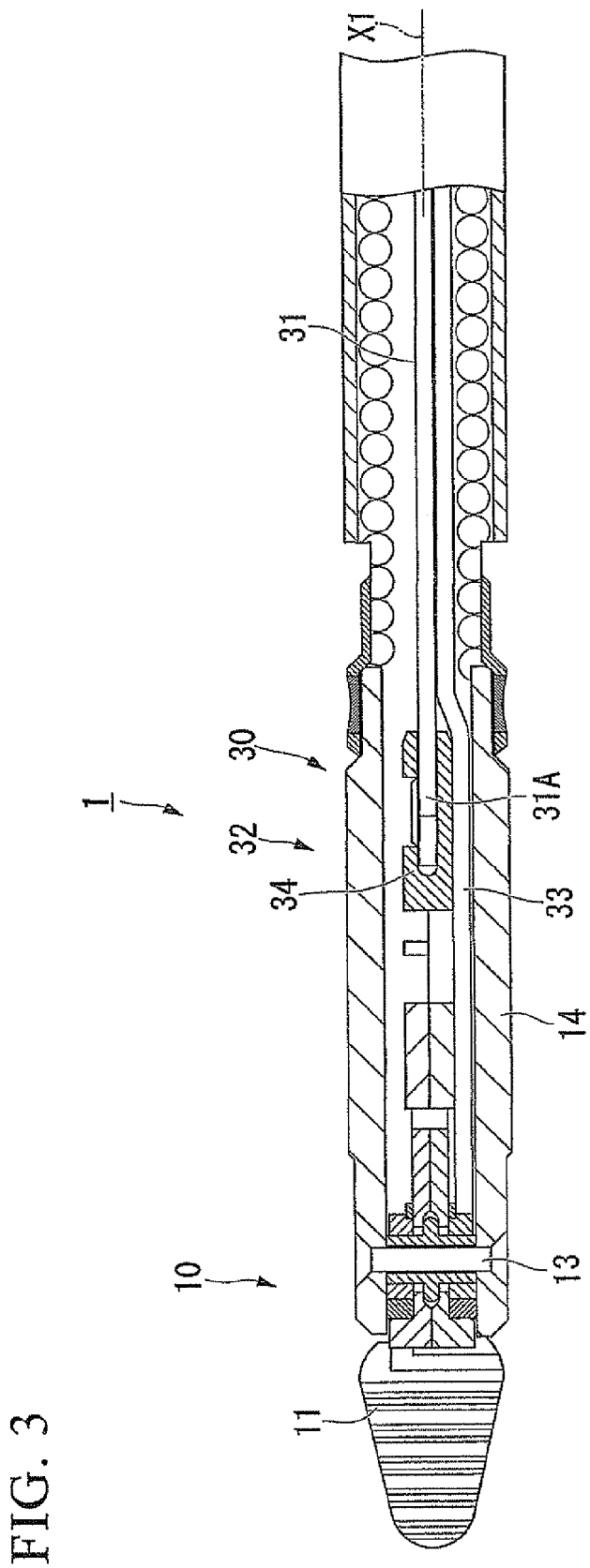
FIG. 3 is a cross-sectional view illustrating the vicinity of the treatment section.

FIG. 2 is a diagram illustrating the vicinity of the treatment section 10 of the treatment tool 1 except for the cover 14, and FIG. 3 is a cross-sectional view illustrating the vicinity of the treatment section 10 at a different angle. As shown in FIGS. 2 and 3, the connection section 30 includes an operation wire 31, a link mechanism 32 that is attached to the front end of the operation wire 31, and a regulation wire (a regulation portion) 33 that guides a forward and backward movement operation of the link mechanism 32. The operation wire 31 has a general configuration, a front-end-side first end 31A is connected to the link mechanism 32, and a base-end-side second end 31B (refer to FIG. 1) is connected to the slider 22 of the operation section 20.

The link mechanism 32 includes a connection member 34 that is attached to the front end of the operation wire 31 and a pair of link members including a first link member 35 and a second link member 36 respectively connecting the connection member 34 to the pair of clamp members 11 and 12.

The front end side of the connection member 34 is provided with two link rotary shafts 34A and 34B. The base ends of the first link member 35 and the second link member 36 are respectively connected to the link rotary shafts 34A and 34B through pins 37 so as to be rotatable. Further, the connection member 34 is provided with a groove 34C that extends in parallel with the axis X1 of the operation wire 31.

The link rotary shafts 34A and 34B are distant from the axis X1 of the operation wire by the same distance (substantially the same distance), and face each other with the axis X1 interposed therebetween. The axes of two pins 37 are parallel (substantially parallel) to each other, and two link rotary shafts 34A and 34B are disposed to be parallel to each other.

The front ends of the link members 35 and 36 are respectively connected to the base ends of the first clamp member 11 and the second clamp member 12 so as to be rotatable. In the state where the pair of clamp members 11 and 12 are closed, the link members 35 and 36 are set to be parallel to each other.

In the regulation wire 33, a first end 33A is connected to the clamp rotary shaft 13, and a second end (not shown) is connected to the body 21 of the operation section 20 through the insertion section 40. The regulation wire 33 is disposed to be parallel (substantially parallel) to the axis X1 of the operation wire 31 so that it passes through the inside of the groove 34c of the connection member 34.

Figure 4:
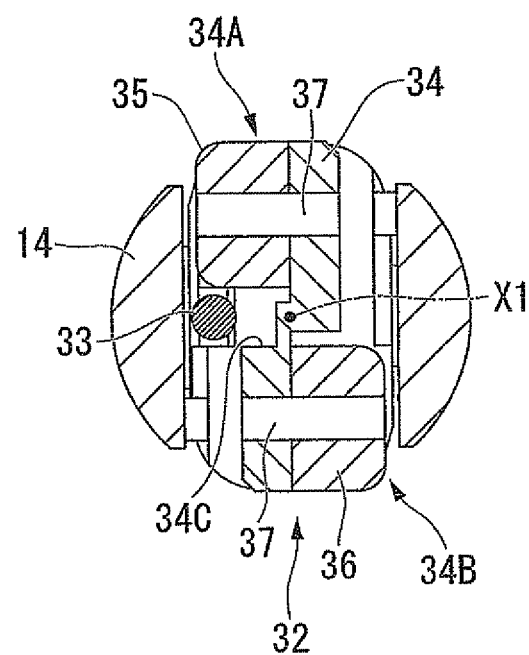
FIG. 4 is a cross-sectional view taken along the line A-A of FIG. 2.

FIG. 4 is a cross-sectional view taken along the line A-A of FIG. 2. As shown in FIG. 4, the cross-sectional shape of the surface perpendicular to the axis X1 of the connection member 34 is formed in a crank shape so that the portion provided with the link rotary shaft 34A and the portion provided with the link rotary shaft 34B intersect each other with the axis X1 interposed therebetween. Accordingly, the maximum thickness dimension of the link mechanism 32 is close to the sum of the thickness of the connection member 34 and the thickness of each of the link members 35 and 36 in any one of the link rotary shafts 34A and 34B, and is suppressed to be a thickness corresponding to two members.

The insertion section 40 includes a coil sheath 41 through which the operation wire 31 is inserted and a tube sheath 42 through which the coil sheath 41 is inserted.

The coil sheath 41 may appropriately adopt the general configuration. The cover 14 is attached to the front end of the coil sheath 41, and the body 21 of the operation section 20 is fixed to the base end thereof.

Figure 5:
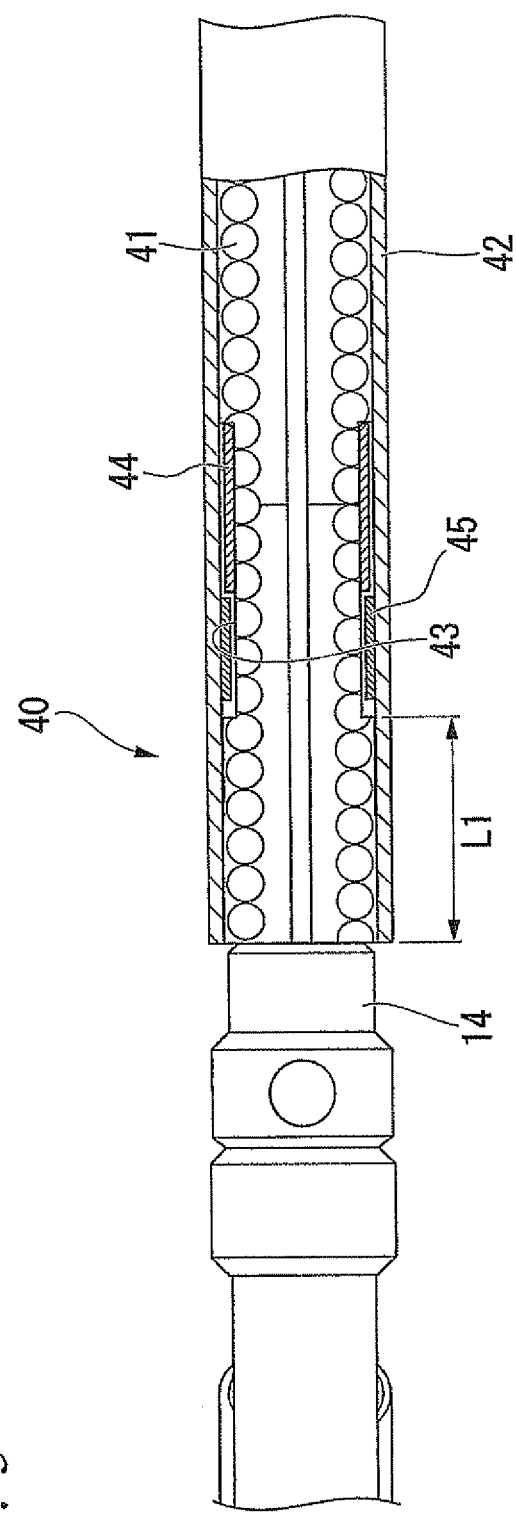
FIG. 5 is a cross-sectional view illustrating a part of an insertion section of the endoscope treatment tool.

As shown in FIG. 5, a small diameter portion 43 with a small outer diameter is formed by cutting the outer peripheral surface of the base end portion of the coil sheath 41 distant from the front end thereof by a predetermined length L1. The coil sheath 41 is divided into two parts in the small diameter portion 43, and the two parts are formed as an integral coil sheath by soldering through a connection ring 44 attached to the small diameter portion 43.

The tube sheath 42 may also appropriately adopt the general configuration using a resin or the like. Although the base end of the tube sheath 42 is inserted into an opening provided at the front end of the body 21, the tube sheath is rotatable relative to the body 21. A ring member (a forward and backward movement suppressing member) 45 fitted to the small diameter portion 43 of the coil sheath 41 is press-inserted into the tube sheath 42. In such a press-inserted state, the inner diameter of the ring member 45 is set to be smaller than the basic outer diameter (the outer diameter of a portion other than the small diameter portion 43) of the coil sheath 41 and the outer diameter of the connection ring 44. Further, the inner diameter of the ring member 45 is larger than the outer diameter of the small diameter portion 43, so that a clearance is ensured therebetween.

With such a configuration, the coil sheath 41 and the tube sheath 42 are relatively rotatable about the axis and are not relatively movable in the axial direction. In order to realize the above-described configuration, one coil sheath provided with the small diameter portion 43 is divided into two parts by cutting it at the small diameter portion 43. Then, the cut coil sheaths are connected to each other using the connection ring 44 while the ring member 45 is fitted into the small diameter portion of the front-end-side coil sheath. Subsequently, the coil sheath 41 having the ring member 45 attached thereto is inserted into the tube sheath 42, and the ring member 45 is press-inserted into the tube sheath 42. Accordingly, the insertion section 40 of the treatment tool 1 is completed.

The predetermined length L1 may be appropriately set, however, it is desirable that the insertion section 40 between the ring member 45 and the connection member 34 of the connection section 30 be set to a length causing sufficient flexure thereof, for example, 20 millimeters (mm) or more in order to shorten the front-end-side rigid length (to be described later) of the treatment tool 1.

An operation during use of the treatment tool 1 with the above-described configuration will be described.

First, an endoscope (not shown) is inserted into the body of a patient, and the front end of the endoscope is made to advance to the vicinity of tissue (a subject tissue) inside a body cavity of a treatment subject.

Subsequently, the slider 22 is retracted with respect to the body 21 of the operation section 20 to close the pair of clamp members 11 and 12, and the insertion section 40 is inserted into a clamp channel of the endoscope. Then, the treatment section 10 is made to protrude from the front end of the clamp channel. At this time, since the treatment section 10 of the front end of the treatment tool 1 and a part of the connection section 30 covered by the cover 14 is distant from a portion provided with the ring member 45 of the insertion section 40 by the predetermined length L1, the flexibility of the insertion section 40 therebetween is maintained. As a result, even when the endoscope moves in a meandering shape inside the body cavity, the treatment tool 1 may be appropriately inserted into the clamp channel of the endoscope while being satisfactorily bent to follow the shape.

Figure 6:
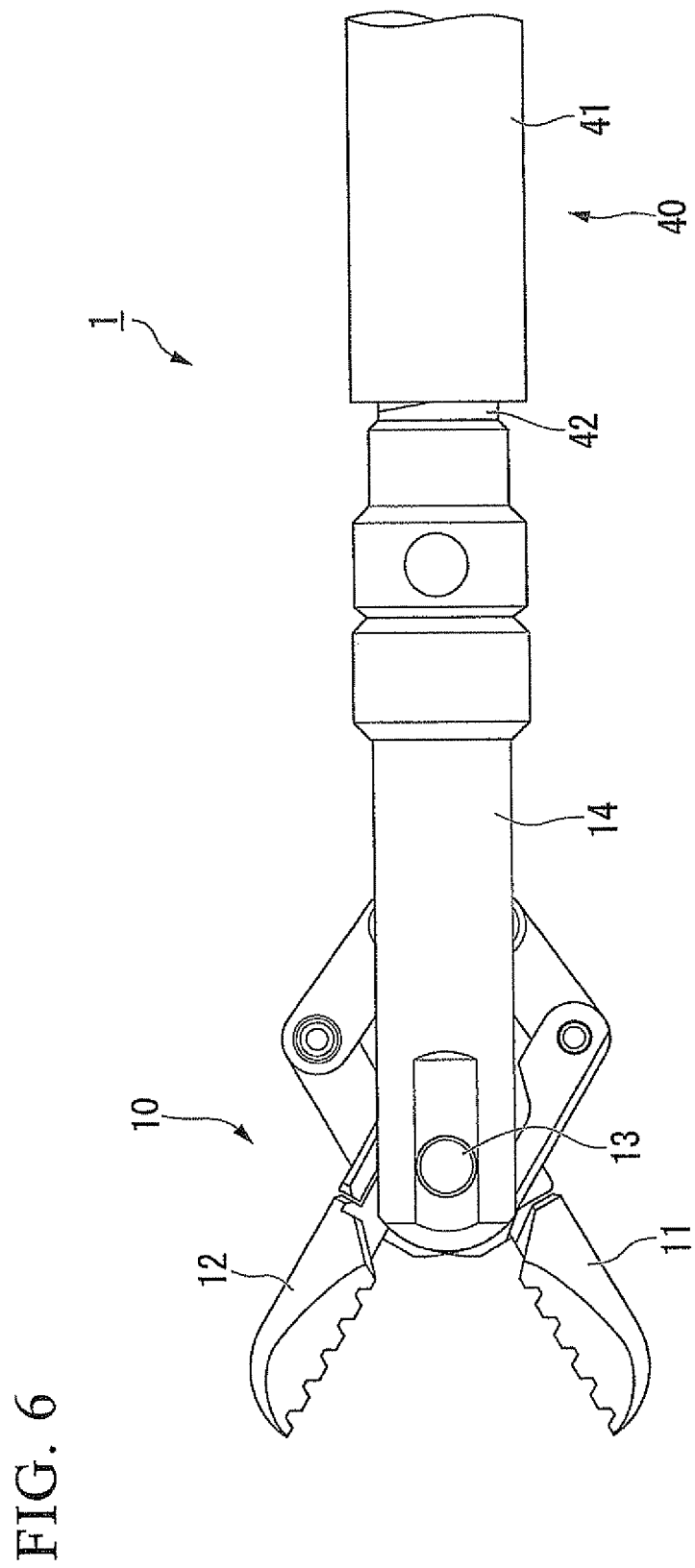
FIG. 6 is a diagram illustrating an operation when using the endoscope treatment tool.

When performing the treatment, the slider 22 is made to advance with respect to the body 21. Then, the operation wire 31 connected to the slider 22 advances with respect to the coil sheath 41. As described above, since the clamp rotary shaft 13 is supported by the cover 14 attached to the coil sheath 41, the first clamp member 11 and the second clamp member 12 respectively rotate about the center of the clamp rotary shaft 13, so that the treatment section 10 is opened as shown in FIG. 6.

At this time, the operation wire 31 and the connection member 34 attached to the front end thereof moves forward and backward along the regulation wire 33 disposed to be parallel to the axis X1 of the operation wire 31 in a manner such that the groove 34C engages with the regulation wire 33. Therefore, the relative movement direction of the operation wire 31 and the connection member 34 with respect to the clamp rotary shaft 13 is regulated, and the connection member 34 is operated to move forward and backward while being suppressed from being deviated from the axis X1, so that the pair of clamp members 11 and 12 is satisfactorily opened and closed.

The user performs a desired treatment on the subject tissue by moving the slider 22 forward and backward to open and close the pair of clamp members 11 and 12 of the treatment section 10. If necessary, the body 21 is rotated about the axis to rotate the treatment section 10 and adjust the positional relationship between the subject tissue and the opening and closing surfaces of the pair of clamp members 11 and 12.

According to the treatment tool 1 of the embodiment, the connection member 34 is provided with two link rotary shafts 34A and 34B distant from the axis X1 of the operation wire 31, and the link rotary shafts are respectively connected to the first link member 35 and the second link member 36. Therefore, the thickness dimension of the connection portion between the connection member 34 and each of the link members 35 and 36 in the extension direction of each of the link rotary shafts 34A and 34B corresponds to the thickness of two members being the sum of one of the link members 35 and 36 and the connection member 34. As a result, the front-end-side area including the treatment section may be further decreased in diameter compared to the existing structure in which two link members are connected to each other through the same rotary shaft.

Further, the rigid treatment section 10 provided at the front end side of the treatment tool 1 and a part of the connection section 30 are disposed to be separated by the predetermined length L1 from the ring member 45 connecting the coil sheath 41 and the tube sheath 42 in the insertion section 40 to each other to be relatively rotatable. For this reason, when the rigid treatment section 10 and the like are adjacent to the ring member 45, the front-end-side rigid length of the treatment tool 1 being the sum thereof in the axial direction may be substantially shortened. Therefore, the treatment tool may be satisfactorily inserted into the endoscope.

In the existing treatment tool, the structure of connecting the coil sheath 41 and the tube sheath 42 to be relatively rotatable is provided near the front end of the tube sheath in many cases. As a result, the length of the rigid front end of the treatment tool is lengthened, so that there is a problem in that the treatment tool is not easily inserted into the clamp channel and a large capability is needed to insert and extract the treatment tool into and from the endoscope. The structure of the insertion section 40 of the treatment tool 1 of the embodiment solves this problem.

Next, a second embodiment of the invention will be described by referring to FIGS. 7 to 9. A treatment tool 51 of the embodiment is different from the treatment tool 1 of the first embodiment in that power is supplied to the treatment section through the regulation wire.

Furthermore, in the following description, the same reference numerals will be given to the same components as those of the treatment tool of the above-described embodiment, and the description thereof will not be repeated.

Figure 7:
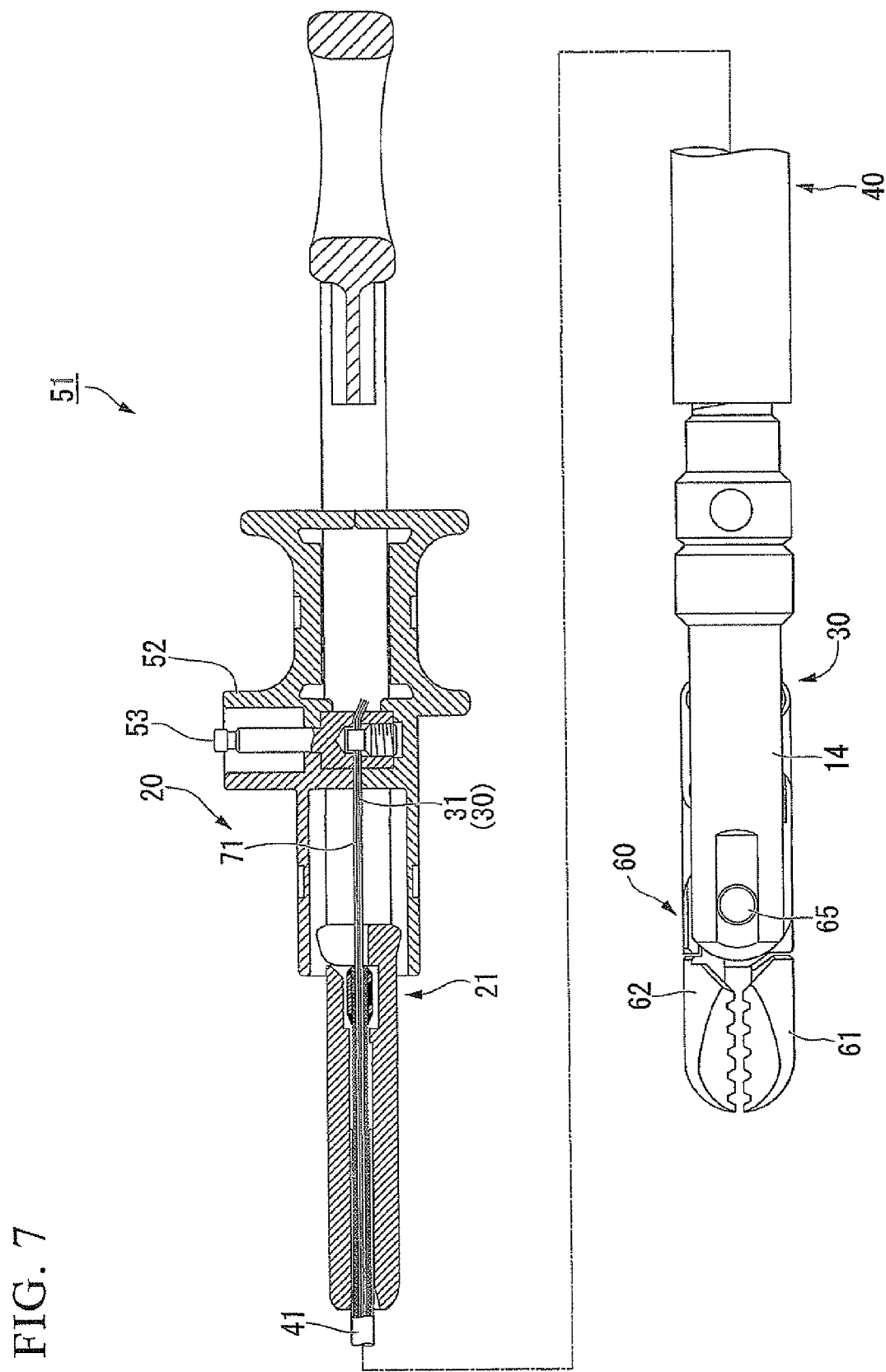
FIG. 7 is an overall diagram illustrating an endoscope treatment tool of a second embodiment of the invention.

FIG. 7 is an overall diagram illustrating the treatment tool 51. A slider 52 provided in the operation section 20 instead of the slider 22 is provided with a plug 53 that is connected to a high frequency power supply (not shown).

Figure 8:
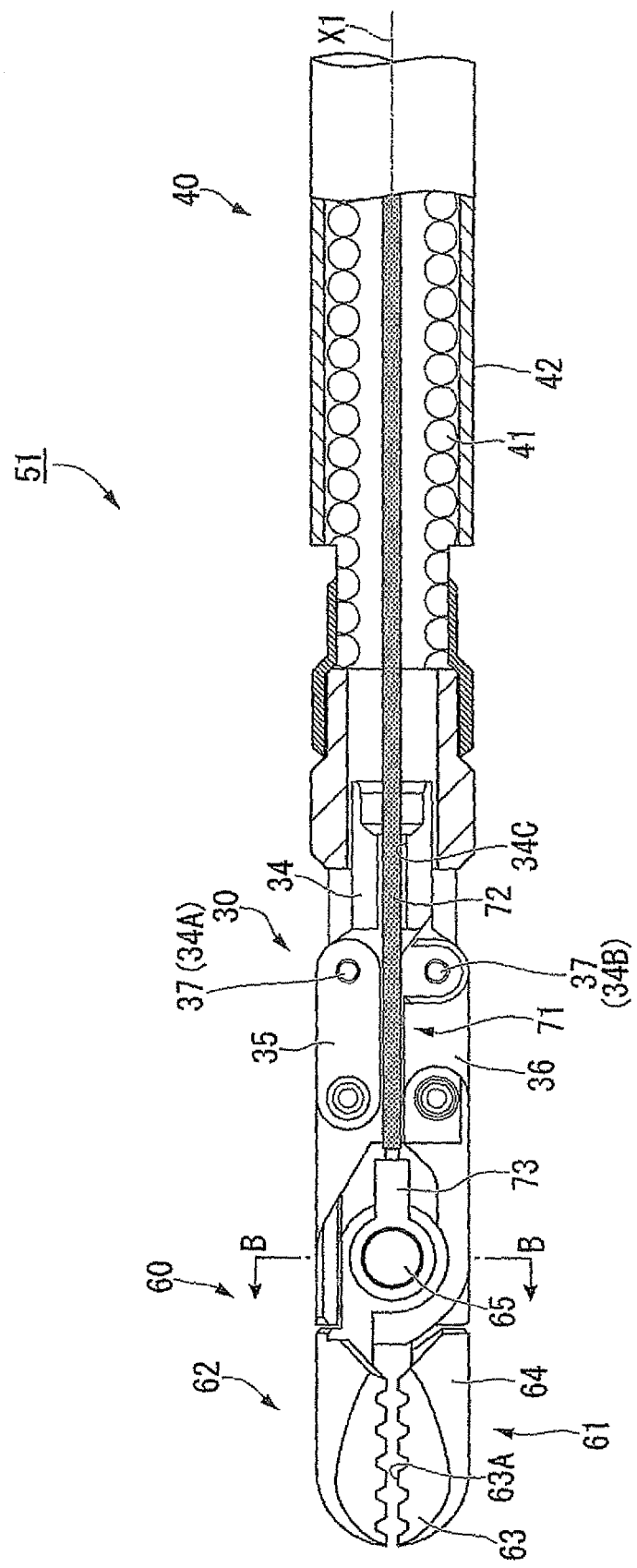
FIG. 8 is a diagram illustrating the vicinity of a treatment section of the endoscope treatment tool except for a cover.

FIG. 8 is a diagram illustrating the vicinity of the treatment section 60 of the treatment tool 51 except for the cover 14. The treatment section 60 includes a first clamp member 61 and a second clamp member 62 instead of the pair of clamp members 11 and 12.

The second clamp member 62 is formed of a ceramic member such as zirconia or alumina or a resin such as polytetrafluorethylene (PTFE) or polyether ether ketone (PEEK: registered trade mark), and has an insulation property.

Furthermore, instead of such a configuration, the second clamp member 62 may be formed by coating the entire surface of the core formed of metal such as stainless steel with the insulation member or insulation coating.

On the other hand, the first clamp member 61 includes an electrode portion 63 of which an electrode surface 63A formed of a conductor such as stainless is exposed and an insulation portion 64 that is provided to cover a part of the electrode portion 63. As shown in FIG. 8, it is desirable that the electrode surface 63A be disposed in at least the opening and closing surface facing the pair of clamp members 61 and 62 contacting the tissue inside the body cavity during treatment. Further, it is desirable that the area of the electrode surface 63A be small since energy concentration is easily performed in a small area.

The insulation portion 64 may be formed by coating a part of the surface of the electrode portion 63 using the same insulation member as that of the second clamp member 62 or performing insulation coating thereon. The insulation portion 64 is provided to prevent current supplied to the electrode portion 63 from leaking to the metallic section such as the treatment section 60 and the connection section 30. For example, all portions that may contact the link members 35 and 36 or the cover 14 are coated by the insulation portion. Therefore, in the first clamp member 61, the surface of the portion near the base end in relation to a clamp rotary shaft 65 to be described later is almost completely coated with the insulation portion.

Figure 9:
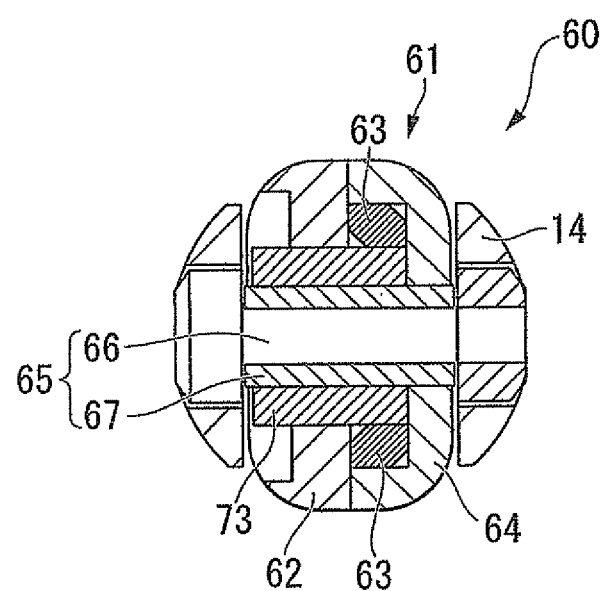
FIG. 9 is a cross-sectional view taken along the line B-B of FIG. 8.

FIG. 9 is a cross-sectional view taken along the line B-B of FIG. 8. As shown in FIG. 9, the clamp rotary shaft 65 connecting the pair of clamp members 61 and 62 to be relatively rotatable includes a core body 66 formed of a conductor and a cylindrical portion (an insulation layer) 67 coating the outer peripheral surface of the core body 66 for insulation. A cylindrical portion 67 may be formed as a member formed of an insulation material or an insulation layer formed of an insulation coating. Any of them may be adopted.

The connection section 30 is provided with a regulation wire 71 instead of the regulation wire 33. The base end (the second end) of the regulation wire 71 is electrically connected to the plug 53, and the regulation wire 71 serves as a power feeding wire that supplies a high frequency current to the electrode portion 63 of the treatment section 60. The regulation wire 71 is provided with an insulation coating 72 formed throughout the entire length except for both ends thereof so that a current does not flow to a metallic portion other than the electrode portion 63.

A cylindrical rotary contact member 73 is attached to the front end (the first end) of the regulation wire 71. As shown in FIG. 9, the rotary contact member 73 is fitted to the outside of the cylindrical portion 67 so as to be coaxial with the clamp rotary shaft 65. Then, the rotary contact member is electrically connected to a part of the electrode portion 63 exposed to face the outer peripheral surface of the cylindrical portion 67.

With such a structure, the front end of the regulation wire 71 is rotatably attached to the clamp rotary shaft 65, so that a high frequency current may be supplied only to the electrode portion 63 of the first clamp member 61. Further, when seen from the axial direction of the link rotary shafts 34A and 34B as shown in FIG. 8, the regulation wire 71 is disposed between the first link member 35 and the second link member 36, and the regulation wire 71 does not overlap each of the link members 35 and 36.

With the above-described structure, the treatment tool 51 is formed as a monopolar (monopole type) high frequency treatment tool.

An operation in use of the treatment tool 51 with the above-described configuration will be described.

First, an endoscope (not shown) is inserted into the body of a patient in contact with a general opposite polar plate (not shown), and the front end of the endoscope is made to advance to the vicinity of the tissue inside the body cavity of the treatment subject. Then, in the same order as that of the treatment tool 1 of the first embodiment, the treatment section 60 is made to protrude from the clamp channel, and a high frequency power supply (not shown) is connected to the plug 53 through a power supply cable (not shown).

When the user pulls the slider 52 to be away from the treatment section 60 while the tissue is positioned between the pair of opened clamp members 61 and 62 of the treatment section 60, the front ends of the pair of clamp members 61 and 62 are closed, so that the subject tissue becomes close to the treatment section 60 and the electrode surface 63A contacts the subject tissue.

In this state, when the user supplies a high frequency current from the high frequency power supply, the high frequency current is supplied to the electrode portion 63 through the regulation wire 71, and the subject tissue is cauterized at the electrode surface 63A.

After the treatment is ended, the user extracts the treatment tool 51 from the clamp channel, extracts the endoscope to the outside of the body, and ends the surgical operation.

According to the treatment tool 51 of the embodiment, since the regulation wire 71 is used as a power feeding wire, it is not necessary to perform an insulation process on the link members 35 and 36 and the like and it is possible to more easily and selectively supply a high frequency current to the electrode portion 63 compared to the case where power is fed through the operation wire 31.

Further, since the front end of the regulation wire 71 is rotatably connected to the clamp rotary shaft 65 through the rotary contact member 73, the pair of clamp members 61 and 62 may be appropriately opened and closed without applying an extra force to the clamp member.

Furthermore, since the rotary contact member 73 does not move with the opening and closing operation of the pair of clamp members 61 and 62, the rotary contact member is not exposed to the outside of the cover 14 during the treatment. Therefore, it is possible to appropriately suppress the regulation wire 71 from unnecessarily contacting the inside of the body cavity and the electrical leakage thereof.

Furthermore, since the rotary contact member 73 is fitted to the outside of the cylindrical portion 67 of the clamp rotary shaft 65, the rotary contact member is interposed between the cylindrical portion 67 and the electrode portion 63 exposed to face the outer peripheral surface of the cylindrical portion 67, and a part of the electrode portion 63 is positioned at both sides of the rotary contact member 73 in the direction of the axis X1. Therefore, when the slider 52 is pulled to be away from the treatment section 60 in order to close the pair of clamp members 61 and 62 during the treatment, the regulation wire 71 is also pulled toward the operation section 20. Since the rotary contact member 73 is also pulled toward the operation section 20 to be pressed against a part of the electrode portion 63 in accordance with this operation, the rotary contact member 73 and the electrode portion 63 reliably contact each other, and the high frequency current may flow during the treatment.

Furthermore, since the clamp rotary shaft 65 includes the core body 66 formed of a conductor such as metal and the cylindrical portion 67 coating the outer peripheral surface of the core body 66 for insulation, it is possible to easily ensure a rigidity capable of sufficiently withstanding a force exerted when opening and closing the pair of clamp members 61 and 62 while maintaining the insulation of the electrode portion 63.

Further, since the regulation wire 71 serving as a power feeding wire is disposed so as not to overlap the pair of link members 35 and 36 when seen in the axial direction of the link rotary shafts 34A and 34B, the regulation wire 71 may be disposed in a linear shape parallel to the axis X1 of the operation wire 31 through the pair of link members 35 and 36 parallel to each other. As a result, the regulation wire 71 may have both a function of guiding the sliding movement of the connection member 34 of the connection section 30 and a function of supplying power to the electrode portion 63.

Next, a third embodiment of the invention will be described by referring to FIGS. 10 to 12. A treatment tool 81 of the embodiment is different from the treatment tools of the above-described embodiments in that the treatment tool 81 is formed as a bipolar (dipole type) high frequency treatment tool as a whole.

Figure 10:
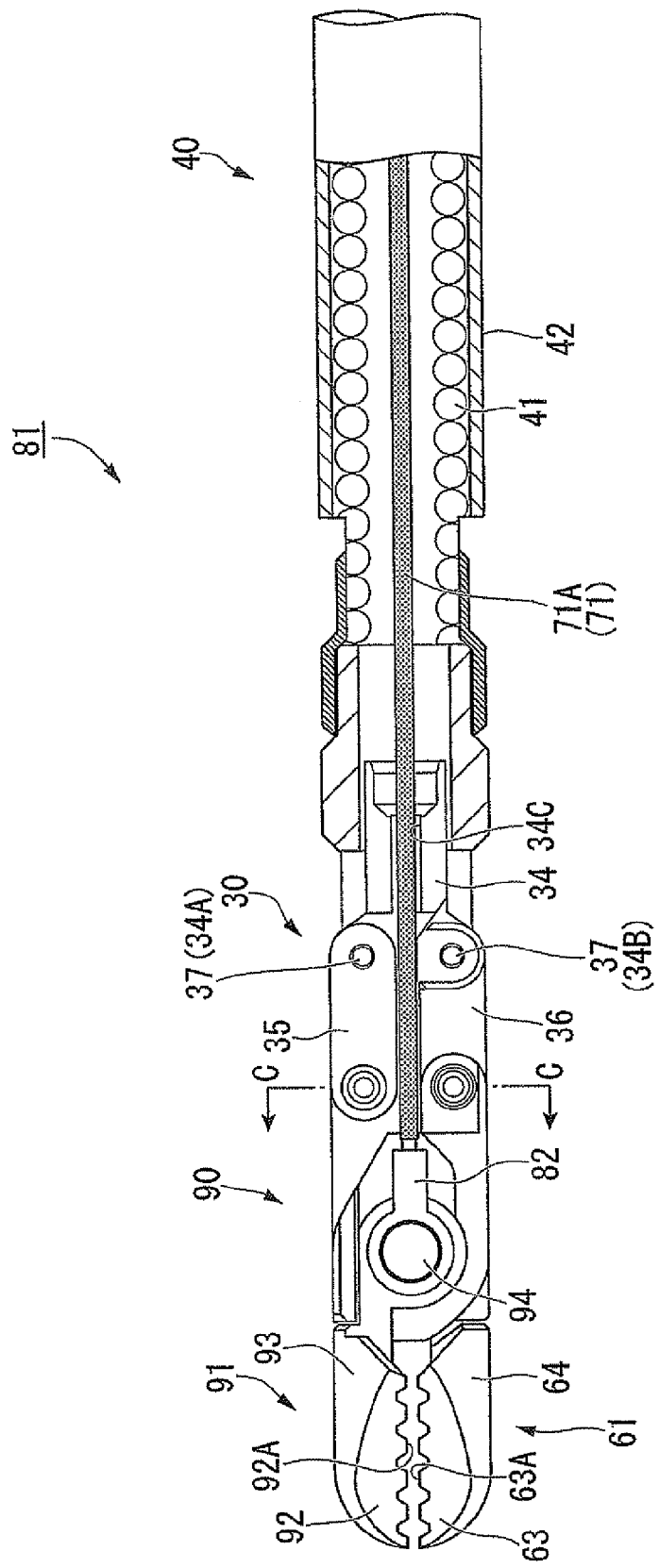
FIG. 10 is a diagram illustrating the vicinity of a treatment section of an endoscope treatment tool of a third embodiment of the invention.
Figure 11:
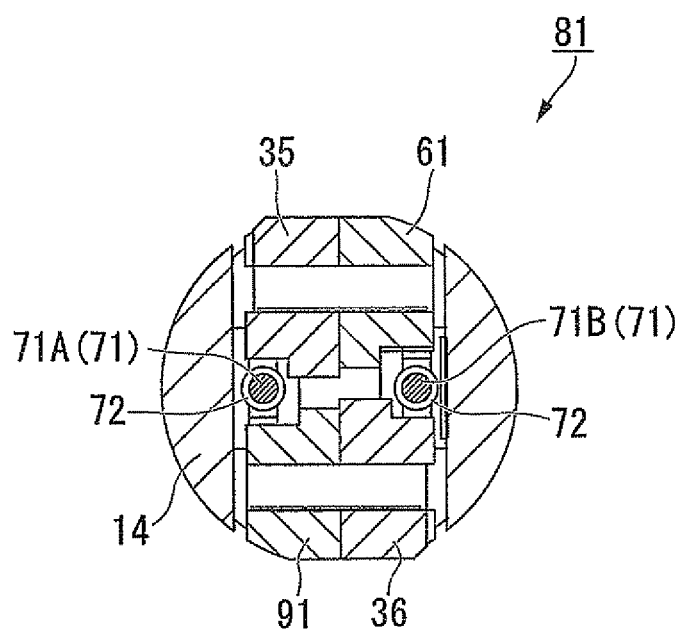
FIG. 11 is a cross-sectional view taken along the line C-C of FIG. 10.
Figure 12:
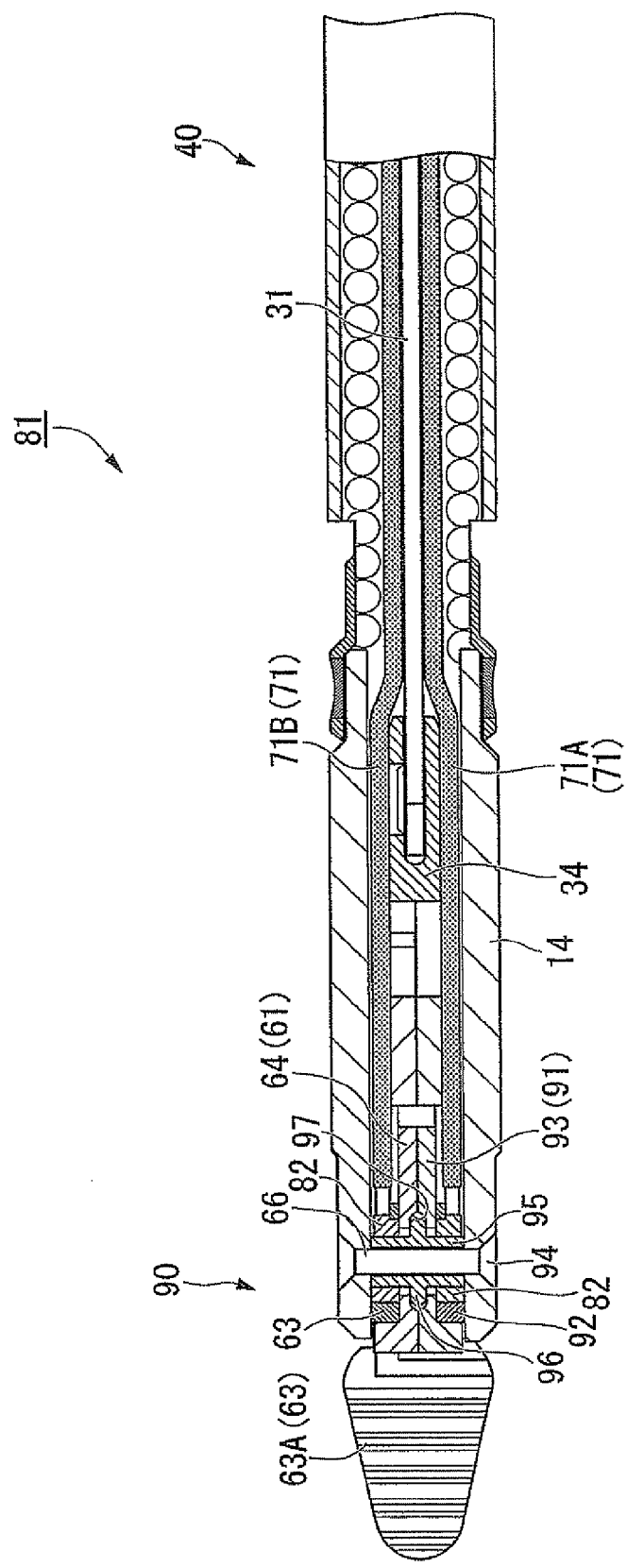
FIG. 12 is a cross-sectional view illustrating the vicinity of the treatment section.

FIG. 10 is a diagram illustrating the vicinity of a treatment section 90 of the treatment tool 81 except for the cover 14, and FIG. 11 is a cross-sectional view taken along the line C-C of FIG. 10. Further, FIG. 12 is a cross-sectional view in the plane parallel to the clamp rotary shaft and the operation wire in the vicinity of the treatment section 90. As shown in FIGS. 10 to 12, in the treatment tool 81, the regulation wire 71 serving as a power feeding wire is connected to two treatment sections 90. Accordingly, the regulation wires are provided at two positions in total of both surfaces of the groove 34C of the connection member 34.

The treatment section 90 includes a pair of clamp members, that is, a first clamp member 61 and a second clamp member 91. The second clamp member 91 has substantially the same structure as that of the first clamp member 61, and includes an electrode portion 92 with an electrode surface 92A and an insulation portion 93. The contact portions of the first clamp member 61 and the second clamp member 91 are respectively coated by the insulation portions 64 and 93 so as to prevent an electrical connection state.

The clamp rotary shaft 94 includes the core body 66 and an insulation cylindrical portion 95. The outer peripheral surface of the cylindrical portion 95 is provided with a flange (a protrusion) 96 that protrudes outward in the radial direction throughout the entire circumference. In the first clamp member 61 and the second clamp member 91 connected to the clamp rotary shaft 94, a part of the surfaces facing each other is cut, and a flange 96 advances to a concave portion 97 formed by the cutting.

A rotary contact member 82 attached to two regulation wires 71 has substantially the same shape as that of the rotary contact member 73 of the second embodiment, but the axial dimension of the cylindrical portion fitted to the outside of the clamp rotary shaft 94 is set to be shorter than that of the rotary contact member 73. As shown in FIGS. 10 and 12, one regulation wire 71A is electrically connected to the electrode portion 92 of the second clamp member 91, and the other regulation wire 71B is electrically connected to the electrode portion 63 of the first clamp member 61. The base ends of the regulation wires 71A and 71B are all connected to a high frequency power supply (not shown), and forms a high frequency current circuit.

The method of using the treatment tool 81 is the same as that of the general bipolar high frequency treatment tool, and the opposite polar plate does not need to be provided. When the user supplies power to the treatment section 90 while the subject tissue is interposed between the pair of clamp members 61 and 91, a high frequency current flows from the electrode surface (for example, the electrode surface 63A) of one clamp member to the electrode surface (for example, the electrode surface 92A) of the other clamp member, so that the subject tissue is cauterized.

Even in the treatment tool 81 of the embodiment, the same advantage as that of the treatment tool 1 of the first embodiment may be obtained. Furthermore, a power feeding treatment may be performed by appropriately opening and closing the pair of clamp members in the same manner as the treatment tool 51 of the second embodiment.

Furthermore, the flange 96 is provided in the cylindrical portion 95 of the clamp rotary shaft 94, and the concave portion 97 is formed at the surface facing the pair of clamp members 61 and 91. Accordingly, since the creeping distance between the electrode portion 63 of the first clamp member 61 and the electrode portion 92 of the second clamp member 91 becomes longer, the insulation therebetween may be more reliably performed.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

Figure 13:
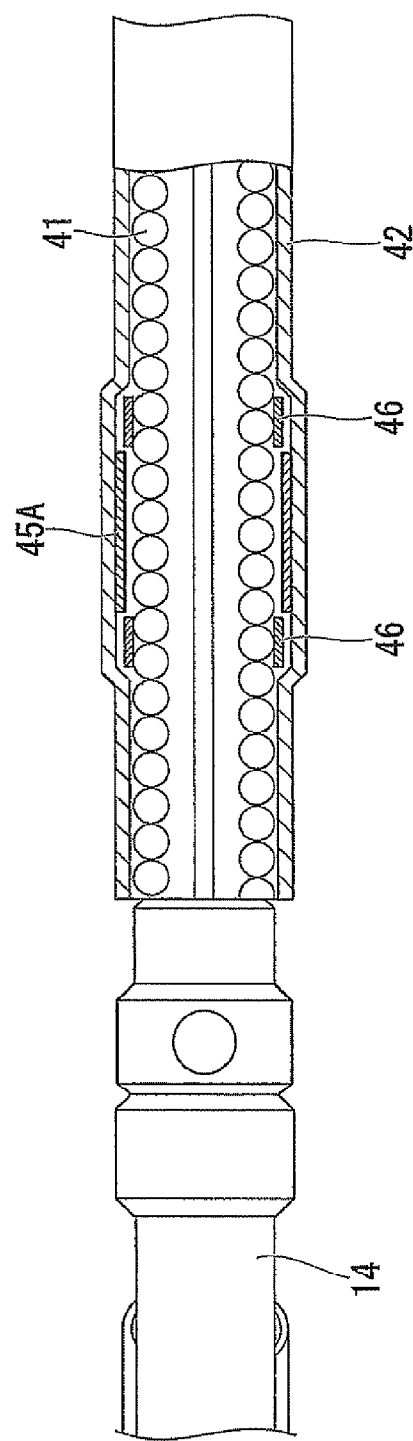
FIG. 13 is a cross-sectional view illustrating a part of an insertion section of an endoscope treatment tool of a modified example of the invention.

For example, in the above-described embodiments, an example has been described in which the small diameter portion 43 is provided in the coil sheath 41 and the ring member 45 is attached to the small diameter portion 43 so that the coil sheath 41 and the tube sheath 42 are relatively rotatable and are not relatively movable in the axial direction. This method has a merit in that the coil sheath and the tube sheath may be assembled without increasing the diameter of the insertion section. However, instead of this method, a method like a modified example shown in FIG. 13 may be adopted, in which the small diameter portion is not formed in the coil sheath 41, and a stopper ring 46 with an outer diameter larger than the inner diameter of the ring member 45A is attached to the outer periphery of the coil sheath 41 by soldering or the like to be positioned at both sides of the ring member 45A press-inserted into the tube sheath 42 in the axial direction.

In this configuration, the diameter of the portion used for the attachment of the ring member 45A or the stopper ring 46 increases compared to the case where the small diameter portion is provided. However, in the case of the treatment tool having few limitations on the diameter dimension, there is a merit in that the coil sheath 41 does not need to be cut and the coil sheath 41 and the tube sheath 42 may be assembled with a smaller number of processes.

Furthermore, in this case, a configuration may be adopted in which the dimensional relationship between the ring member 45A and the stopper ring 46 is reversed, the stopper ring 46 is press-inserted into the tube sheath, and the ring member 45A is fixed to the coil sheath 41.

Figure 14:
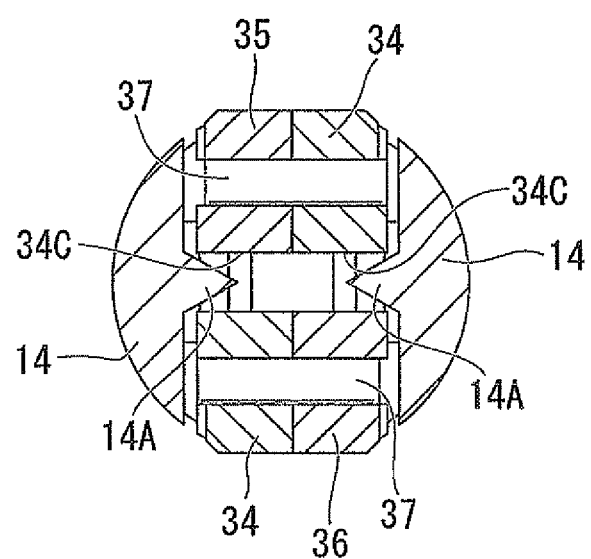
FIG. 14 is a cross-sectional view illustrating a connection section of the endoscope treatment tool of the modified example of the invention.

Further, in the above-described embodiments, an example has been described in which the regulation portion is provided to regulate the rotation of the connection member about the axis using the regulation wire. When the regulation wire is not used as the power feeding wire, instead of this configuration, a configuration may be adopted like a modified example shown in FIG. 14, in which a protrusion 14A is formed in the cover 14 to protrude toward the connection member 34, and the protrusion engages with the groove 34C of the connection member 34 to regulate the rotation of the connection member and the operation wire about the axis.

At this time, only one pair of the protrusion 14A and the groove 34A may be provided at one side.

Furthermore, the shape of the connection member provided at the front end of the operation wire is not also limited to those of the above-described embodiments. For example, one link rotary shaft may be provided, and both base ends of the pair of link members may be fixed to the link rotary shaft.

Further, the pair of link members connected to two link rotary shafts may be disposed to intersect each other while the pair of clamp members is closed.

In this case, since the front end of the regulation wire is not easily connected to the clamp rotary shaft, the front end of the regulation wire may be fixed to the cover 14 or the like at a position near the operation section in relation to the clamp rotary shaft.

Furthermore, the structure and the configuration of the above-described embodiment may be appropriately combined with each other.

According to one type of the endoscope treatment tool of the invention, the clamp member may be reliably opened and closed.

What is claimed is:

1. An endoscope treatment tool comprising:
   a pair of clamp members that is supported by a clamp rotary shaft to be relatively rotatable;
   an operation section that is used to open and close the pair of clamp members;
   an operation wire that connects the pair of clamp members to the operation section;
   a connection member that is provided at the front end of the operation wire and includes at least one link rotary shaft;
   a pair of link members of which a first end is rotatably connected to each end of the pair of clamp members and a second end is rotatably connected to the link rotary shaft; and
   a regulation portion that regulates the connection member and the operation wire in a relative movement direction with respect to the clamp rotary shaft, and that is capable of coming into contact with at least one of surfaces of the pair of link members, the surfaces facing toward the inner side in the direction in which the pair of link members open and close, when the pair of link members rotate about the link shaft,
   wherein the connection member includes a groove formed to be parallel to the axis of the operation wire, and
   wherein the regulation portion engages with the groove to regulate the relative movement direction of the connection member and the operation wire, and to regulate rotations of the pair of link members being over a position in which the pair of link members come into contact with the regulation member in a direction in which the pair of link members comes close to the regulation member.

2. The endoscope treatment tool according to claim 1, wherein the regulation portion is a regulation wire disposed to be parallel to the axis of the operation wire.

3. The endoscope treatment tool according to claim 2,
   wherein at least one of the pair of clamp members includes an electrode portion to which power is fed and an insulation portion that coats at least a part of the electrode portion, and
   wherein a first end of the regulation wire is electrically connected to the electrode portion, and a second end of the regulation wire is connected to a power supply.

4. An endoscope treatment tool comprising:
   a pair of clamp members that is supported by a clamp rotary shaft to be relatively rotatable;
   an operation section that is used to open and close the pair of clamp members;
   an operation wire that connects the pair of clamp members to the operation section;
   a connection member that is provided at the front end of the operation wire and includes at least one link rotary shaft;

a pair of link members of which a first end is rotatably connected to each end of the pair of clamp members and a second end is rotatably connected to the link rotary shaft; and a regulation portion that regulates a relative movement direction of the connection member and the operation wire with respect to the clamp rotary shaft, wherein the connection member includes a groove formed to be parallel to the axis of the operation wire, and wherein the regulation portion engages with the groove to regulate the relative movement direction of the connection member and the operation wire so as to become parallel to an axis of the operation member.

* * * * *